US00PP27920P2

(12) United States Plant Patent
Dobres et al.

(10) Patent No.: US PP27,920 P2
(45) Date of Patent: Apr. 18, 2017

(54) ***PENSTEMON* PLANT NAMED 'NOVAPENBEL'**

(50) Latin Name: *Penstemon hybrida*
Varietal Denomination: Novapenbel

(71) Applicant: CP DELAWARE, INC., Wilmington, DE (US)

(72) Inventors: Michael S. Dobres, San Javier (ES); Sloane M. Scheiber, Parkesburg, PA (US)

( * ) Notice: Subject to any disclaimer, the term of this patent is extended or adjusted under 35 U.S.C. 154(b) by 0 days.

(21) Appl. No.: 14/998,378

(22) Filed: Jan. 7, 2016

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Annette Para
(74) *Attorney, Agent, or Firm* — Buchanan Ingersoll & Rooney PC

(57) ABSTRACT

The new *Penstemon* plant was created by a controlled plant breeding program followed by selection, open pollination, and further selection. The growth habit is compact and upright with strong basal branching and excellent vigor. Attractive purple flowers with a lighter purple throat on sturdy stems are formed. There is no vernalization requirement for flowering. Dark green ornamental foliage is displayed. The plant readily roots from stem cuttings and is well suited for providing attractive ornamentation.

2 Drawing Sheets

Botanical/commercial classification: *Penstemon hybida/ Penstemon* Plant.

Varietal denomination: cv. Novapenbel.

SUMMARY OF THE INVENTION

*Penstemon* plants, sometimes known as Beard Tongue, are herbaceous perennials which provide colorful flowers during the summer.

The new *Penstemon* plant of the present invention was created and discovered at West Grove, Pa., U.S.A. The female parent (i.e., seed parent) was the *Penstemon mexicali* 'Pike's Peak Purple' cultivar (non-patented in the United States). The male parent (i.e., pollen parent) was an unnamed and non-patented breeder seedling selected from second generation seedlings from the cross of *Penstemon smallii* 'Violet Dusk' cultivar (non-patented in the United States) and *Penstemon hirsutus* 'Pygameus' cultivar (non-patented in the United States). Seedlings from the cross of 'Violet Dusk' and 'Pygameus' underwent open pollination and the male parent was selected from the resulting seedlings. This breeder seedling was selected for increased branching, increased number of inflorescences and extended bloom time. A single plant of the new cultivar was selected from the cross of the female and male parents. Had this new plant not been selected and preserved it would have been lost to mankind.

The parentage of the new cultivar can be summarized as follows:

'Pike's Peak Purple'×[('Violet Dusk'×'Pygameus')× Open Pollination].

It was found that the new *Penstemon* plant displays the following combination of characteristics:

(a) displays a compact and upright growth habit with strong basal branching and excellent vigor,
(b) is lacking a vernalization requirement for flowering, (c) abundantly forms attractive purple flowers with a lighter purple throat on sturdy stems,
(d) forms ornamental dark green foliage, and
(e) is well suited for providing attractive ornamentation.

During observations to date, the plant has been found to be hardy at U.S.D.A. Hardiness Zone No. 6. Trimming of the plant promotes further flowering. Tolerance to insects is typical of Penstemon during observations to date.

The new cultivar well meets the needs of the horticultural industry and can be grown to advantage as a perennial garden plant to provide colorful ornamentation. The plant performs well when grown along borders or sidewalks as well as in containers.

Plants of the new cultivar can be readily distinguished from other *Penstemon* cultivars. More specifically, when compared to its 'Pike's Peak Purple' ancestor, the new cultivar displays a more compact growth habit. The blossoms of the 'Violet Dusk' ancestor are of a lighter lavender pink coloration, and the blossoms of the 'Pygameus' cultivar display substantial white coloration.

The new cultivar readily roots from stem cuttings.

The rooting of vegetative cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novapenbel', and will be marketed under the LITTLE BELLS Trademark.

BRIEF DESCRIPTION OF THE PHOTOGRAPHS

The accompanying photographs illustrates typical flowering plants of the new cultivar in color as nearly true as it is reasonably possible make the same in color illustrations of this nature. The plants were approximately two years of age and were being grown outdoors in containers during July 2014 at West Grove, Pa., U.S.A. The plants had been asexually reproduced by the rooting of vegetative cuttings.

DETAILED BOTANICAL DESCRIPTION

Figure 1:
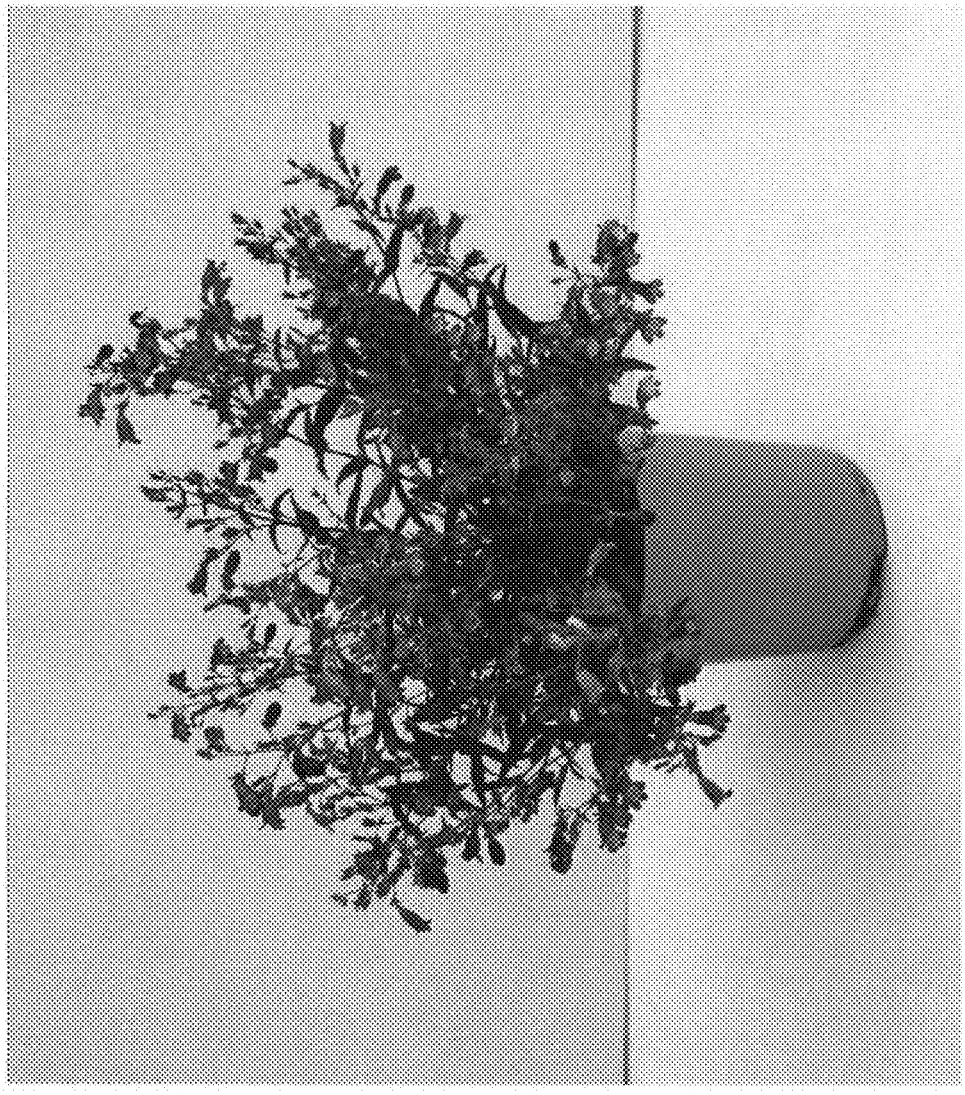
FIG. 1 illustrates the attractive compact and upright growth habit of a flowering plant of the new cultivar.
Figure 2:
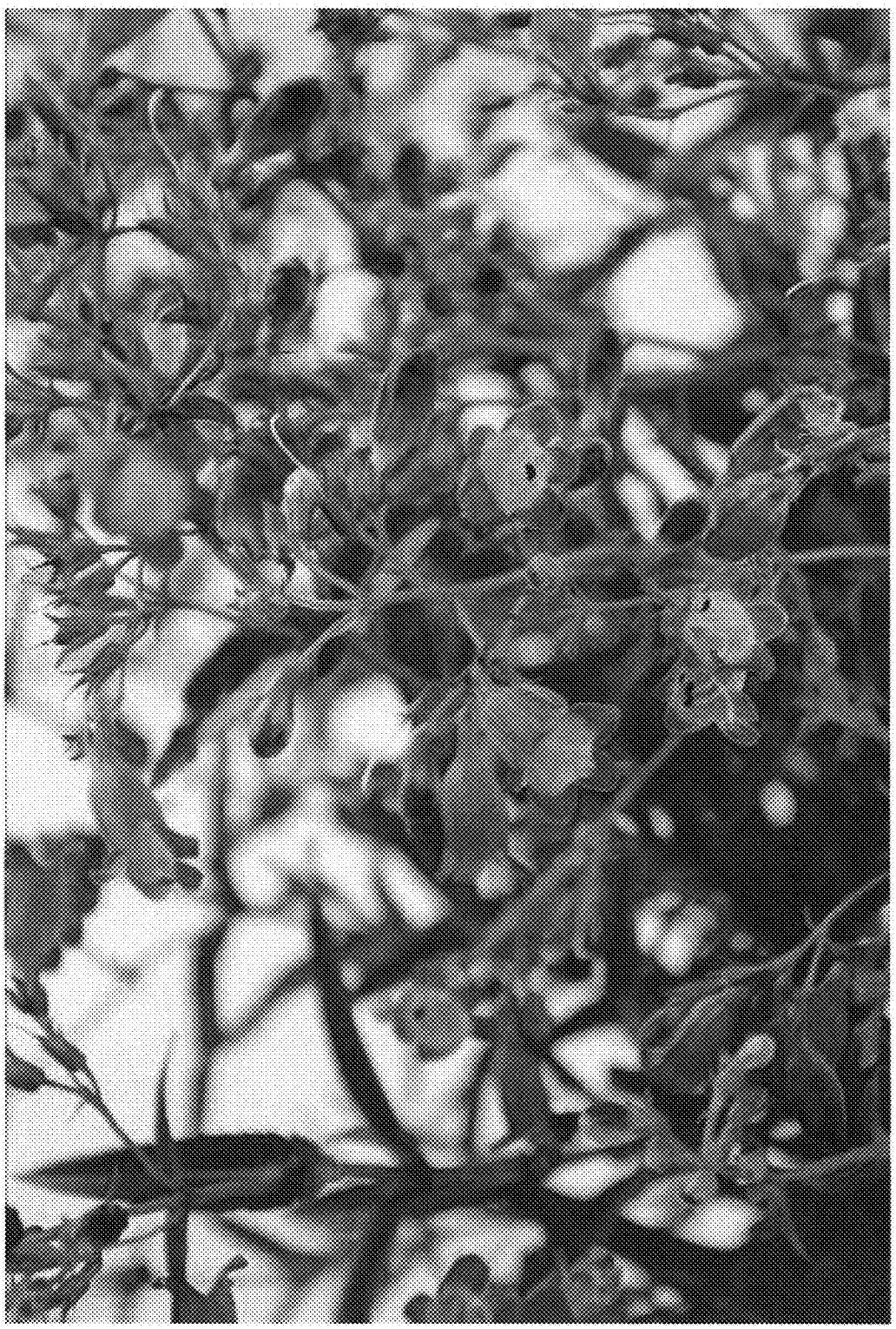
FIG. 2 illustrates a closer view of the purple blossoms in various stages of development as well as the foliage of the new cultivar.

The following is a detailed description while observing one-year-old plants of the new cultivar that were produced by the rooting of vegetative cuttings. Such plants were being grown in containers on their own roots at West Grove, Pa., U.S.A. The chart used in the identification of color is The R.H.S. Colour Chart (1995 Edition) of The Royal Horticultural Society, London, England. Common color terms are to be accorded their customary dictionary significance.

Botanical classification: *Penstemon*, cv. Novapenbel.

*Parents*.—Cross of 'Pike's Peak' and the product of the cross of 'Violet Dusk' and 'Pygameus', followed by selection, open pollination, and further selection.

*Plant type*.—Herbaceous perennial.

Plant:

*Growth habit*.—Compact and upright with considerable branching to form a fountain of branched stems.

*Height*.—Approximately 30 cm on average. This compares to a height of approximately 45 cm on average for the 'Pike's Peak Purple' cultivar under the same growing conditions.

*Spread*.—Approximately 55 cm on average. This compares to a spread of approximately 90 cm on average for the 'Pike's Peak Purple' cultivar under the same growing conditions.

*Vigor*.—Excellent.

Foliage:

*Arrangement*.—Opposite, simple, sessile.

*Shape*.—Lanceolate.

*Apex*.—Acuminate.

*Base*.—Truncate.

*Length*.—Commonly approximately 7.5 cm on average.

*Width*.—Commonly approximately 1.2 cm on average.

*Texture*.—Glabrous on the upper and under surfaces.

*Aspect*.—Approximately 80 degrees from the stem.

*Color*.—On the upper surface near Green Group 137A, and on the lower surface near Green Group 137C.

*Margins*.—Denticulate.

*Venation*.—Pinnate.

Inflorescence:

*Season*.—Commonly May through frost.

*Type*.—Thyrse.

*Buds*.—Shape: closed tubular and bulging. Size: during early bud stage approximately 1 cm in length and approximately 4 mm in width on average, during the medium bud stage approximately 1.5 cm in length and approximately 5 mm in width on average, and during late bud stage approximately 2 cm in length and approximately 7 mm in width on average. Color: during the early bud stage near Yellow-Green Group 145B, during the medium bud stage near Purple-Violet Group 81A on the upper side and near Purple-Violet Group 82D on the lower side, and during the late bud stage near Purple-Violet Group 81A on the upper side and on the lower side near Purple-Violet Group 81C.

*Flower*.—Type: Zygomirphic, perfect. Shape: Lobe extended bilabiate. Color: on the outside near Purple Group 77A, and on the inside near Purple-Violet Group 82C. Quantity: free flowering, commonly with approximately 125 flowers on the plant at a given time. Fragrance: none detectable. Length: approximately 2.5 cm on average. Diameter: approximately 1.5 cm on average. Fragrance: none detectable.

*Reproductive parts*.—Stamen number: commonly four fertile and one sterile. Stamen shape: commonly curved downwards at the tip ending in two distinct lobes and attached to upper fused petals. Anther sacs: opposite and opening across the connection of each stamen. Anther size: when unopened approximately 2 mm in length and approximately 1 mm in width, and when open/dehisced approximately 2 mm in length and approximately 0.5 mm in width. Style size: commonly approximately 12 mm in length and less than 0.2 mm in width. Filaments: commonly approximately 1.5 cm in length. Pollen: near White Group 155B in coloration. Pistil size: commonly approximately 1.6 cm on average. Pistil color: near Yellow-Green Group 145C.

*Fruit*.—Type: capsule. Fertility: good. Size: commonly approximately 1 cm in length and approximately 4 mm in width. Color: near Brown Group 200A to 200B.

*Seeds*.—Shape: generally irregular. Size: approximately 1 mm in length and less than 1 mm in width. Color: near Brown Group 200A.

*Peduncle*.—Length: commonly approximately 2.5 cm on average. Diameter: approximately 1 mm on average. Texture: finely pubescent. Color: near Yellow-Green Group 146A mixed with Red-Purple Group 60A.

*Pedicel*.—Length: commonly approximately 2 mm on average. Texture: pubescent. Color: near Yellow-Green Group 146A.

Insect resistance: The tolerance/susceptibility to insects common to *Penstemon* plants appears to be typical during observations to date. Plants of the 'Novapenbel' cultivar have not been observed under all possible environmental conditions to date. Accordingly, it is possible that the phenotypic expression may vary somewhat with changes in light intensity and duration, cultural practices, and other environmental conditions.

We claim:

1. A new and distinct *Penstemon* plant having the following combination of characteristics:

(a) displays a compact and upright growth habit with strong basal branching and excellent vigor, (b) is lacking a vernalization requirement for flowering, (c) abundantly forms attractive purple flowers with a lighter purple throat on sturdy stems, (d) forms ornamental dark green foliage, and (e) is well suited for providing attractive ornamentation; substantially as illustrated and described.

* * * * *